United States Patent
Jung et al.

(10) Patent No.: US 10,464,946 B2
(45) Date of Patent: Nov. 5, 2019

(54) CRYSTALLINE FORMS OF THIENOPYRIMIDINE COMPOUND

(71) Applicant: HANMI PHARM. CO., LTD., Hwaseong-si, Gyeonggi-do (KR)

(72) Inventors: Jae Hyuk Jung, Hwaseong-si (KR); Jong Ouk Baek, Hwaseong-si (KR); Sun Young Jung, Hwaseong-si (KR); Eun Joo Kwak, Hwaseong-si (KR); Hee Cheol Kim, Hwaseong-si (KR); Tae Hee Ha, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/066,341

(22) PCT Filed: Dec. 30, 2016

(86) PCT No.: PCT/KR2016/015536
§ 371 (c)(1),
(2) Date: Jun. 27, 2018

(87) PCT Pub. No.: WO2017/116193
PCT Pub. Date: Jul. 6, 2017

(65) Prior Publication Data
US 2019/0016733 A1    Jan. 17, 2019

(30) Foreign Application Priority Data

Dec. 31, 2015 (KR) .................... 10-2015-0190854

(51) Int. Cl.
*C07D 495/04* (2006.01)
*A61K 39/395* (2006.01)
*A61K 31/55* (2006.01)
*A61P 35/00* (2006.01)

(52) U.S. Cl.
CPC ............ *C07D 495/04* (2013.01); *A61K 31/55* (2013.01); *A61K 39/395* (2013.01); *A61P 35/00* (2018.01)

(58) Field of Classification Search
CPC ...... C07D 495/04; A61K 31/55; A61K 39/395
USPC ...................................... 544/278; 514/252.16
See application file for complete search history.

(56) References Cited

FOREIGN PATENT DOCUMENTS

| KR | 10-2011-0139653 A | 12/2011 |
|---|---|---|
| WO | 2011/162515 A2 | 12/2011 |
| WO | 2015/112705 A2 | 7/2015 |
| WO | 2015/134242 A1 | 9/2015 |
| WO | 2016/025641 A1 | 2/2016 |
| WO | 2016/108623 A1 | 7/2016 |
| WO | 2017074147 A1 | 5/2017 |

OTHER PUBLICATIONS

International Searching Authority, Written Opinion of PCT/KR2016/015536 dated Mar. 31, 2017.
International Searching Authority, International Search Report of PCT/KR2016/015536 dated Mar. 31, 2017.
European Patent Office; Communication dated Apr. 15, 2019 in application No. 16882145.2.
Caira, Mino, "Crystalline Polymorphism of Organic Compounds", Topics in Current Chemistry, vol. 198, 1998, pp. 163-208 (46 pages).

*Primary Examiner* — Deepak R Rao
(74) *Attorney, Agent, or Firm* — Sughrue Mion, PLLC (57) ABSTRACT

The present invention relates to crystalline forms of N-(3-(2-(4-(4-methylpiperazin-1-yl)phenylamino)thieno[3,2-d]pyrimidin-4-yloxy)phenyl)acrylamide, and pharmaceutical compositions containing the same. The crystalline forms can be easily used for the preparation of a pharmaceutical composition containing the same as an active ingredient.

18 Claims, 10 Drawing Sheets

CRYSTALLINE FORMS OF THIENOPYRIMIDINE COMPOUND

CROSS REFERENCE TO RELATED APPLICATIONS

This application is a National Stage of International Application No. PCT/KR2016/015536 filed Dec. 30, 2016, claiming priority based on Korean Patent Application No. 10-2015-019854 filed Dec. 31, 2015.

TECHNICAL FIELD

The present invention relates to crystalline forms of a thienopyrimidine compound and pharmaceutical compositions containing the same. More specifically, the present invention relates to crystalline forms of N-(3-(2-(4-(4-methylpiperazin-1-yl)phenylamino)thieno[3,2-d]pyrimidin-4-yloxy)phenyl)acrylamide, and pharmaceutical compositions containing the same.

BACKGROUND ART

The compound of Formula 1 below, whose compound name is N-(3-(2-(4-(4-methylpiperazin-1-yl)phenylamino)thieno[3,2-d]pyrimidin-4-yloxy)phenyl)acrylamide {INN: 2-propenamide, N-[3-[[2-[[4-(4-methyl-1-piperazinyl)phenyl]amino]thieno[3,2-d]pyrimidin-4-yl]oxy]phenyl]}, is disclosed in PCT application WO 2011/162515. The compound has a selective inhibitory activity for a mutant epidermal growth factor receptor tyrosine kinase

[Formula 1]

Additionally, the above reference discloses the method of preparing the compound of Formula 1.

However, the compound of Formula 1 prepared in the above cited references was prepared as an amorphous solid, which is a form generally less suitable for a large-scale production of pharmaceutical drugs. For example, the thus-prepared form of the compound of Formula 1 was insufficient in the aspects of stability and non-hygroscopicity for pharmaceutical formulations.

Accordingly, there is a need for the development of the compound of Formula 1 in crystalline forms which can fully comply with the strict requirements and details thereof regarding pharmaceutical solid forms and formulations. Additionally, the compound of Formula 1 is preferably in a form that affords facile handling of the product upon synthesis such as ease of filtration and drying, and also for the purpose of economy, preferably enables long-term stable maintenance of a crystalline form without requiring particular storage conditions.

Under these circumstances, the present inventors have made intensive efforts to develop a novel crystalline form of the compound of Formula 1, and have discovered that a particular crystalline form can provide excellent overall physicochemical properties such as stability, non-hygroscopicity, etc., and thus it can be easily used for the preparation of a pharmaceutical composition containing the same as an active ingredient, thereby completing the present invention.

DISCLOSURE OF INVENTION

Technical Problem

An object of the present invention is to provide a crystalline form of the compound of Formula 1, and a pharmaceutical composition containing the same.

Solution to Problem

In order to achieve the above object, in one aspect of the present invention, there are provided crystalline forms of the compound of Formula 1 as shown below:

[Formula 1]

Specific examples of the above crystalline forms are as shown below:

A crystalline form of a compound of Formula 1 having an X-ray powder diffraction (XRPD) pattern comprising peaks at diffraction angles of $2\theta=8.6°\pm0.2°$, $16.0°\pm0.2°$ and $17.2°\pm0.2°$ when irradiated with a Cu—Kα light source. This crystalline form may further comprise diffraction peaks at $2\theta=9.4°\pm0.2°$, $10.3°\pm0.2°$, $13.7°\pm0.2°$, $17.9°\pm0.2°$, $19.7°\pm0.2°$, $22.1°\pm0.2°$, $23.6°\pm0.2°$, and $26.4°\pm0.2°$ when irradiated with a Cu—Kα light source:

A crystalline form of a compound of Formula 1 having an X-ray powder diffraction (XRPD) pattern comprising peaks at diffraction angles of $2\theta=5.3°\pm0.2°$ and $16.2°\pm0.2°$ when irradiated with a Cu—Kα light source. This crystalline form may further comprise diffraction peaks at $2\theta=20.7°\pm0.2°$ when irradiated with a Cu—Kα light source;

A crystalline form of a compound of Formula 1 having an X-ray powder diffraction (XRPD) pattern comprising peaks at diffraction angles of $2\theta=3.8°\pm0.2°$ and $11.6°\pm0.2°$ when irradiated with a Cu—Kα light source. This crystalline form may further comprise diffraction peaks at $2\theta=9.8°\pm0.2°$, $16.9°\pm0.2°$, and $19.8°\pm0.2°$ when irradiated with a Cu—Kα light source; and A crystalline form of a compound of Formula 1 having an X-ray powder diffraction (XRPD) pattern comprising peaks at diffraction angles of $2\theta=11.1°\pm0.2°$, $20.3°\pm0.2°$ and $20.8°\pm0.2°$ when irradiated with a Cu—Kα light source. This crystalline form may further comprise diffraction peaks at $2\theta=14.6°\pm0.2°$, $15.5°\pm0.2°$, $21.0°\pm0.2°$ and $22.2°\pm0.2°$ when irradiated with a Cu—Kα light source.

In another aspect, each crystalline form of the compound of Formula 1 as described herein is in substantially pure form.

the term "substantially pure" as used herein means at least 95% pure, preferably 99% pure, where 95% pure means not more than 5%, and 99% pure means not more than 1%, of any other form of the compound of Formula 1 being present (other crystalline form, amorphous form, etc.).

In another aspect of the present invention, there is provided a pharmaceutical composition containing any one selected from the above crystalline forms and at least one pharmaceutically acceptable carrier and/or diluent.

The pharmaceutical composition can be used for the treatment of cancer induced by epidermal growth factor receptor tyrosine kinase or a mutant thereof.

Advantageous Effects of Invention

The crystalline forms of the compound of Formula 1 according to the present invention have excellent overall physicochemical characteristics, and thus the crystalline forms can be easily used for the preparation of a pharmaceutical composition containing the same as an active ingredient.

MODE FOR THE INVENTION

Hereinafter, the present invention will be described in more detail with reference to the following Examples. However, these Examples are for illustrative purposes only, and the invention is not intended to be limited by these Examples.

Unless otherwise defined, all terms including technical and scientific terms used herein have the same meanings as commonly understood within the context by one of ordinary skill in the art to which the invention belongs. However, unless otherwise specified, the term described below will have the meaning indicated below over the entire specification:

As used herein, the term "about" refers to being within 5% of a particular value or range, and more preferably within 1% to 2%. For example, "about 10%" refers to 9.5% to 10.5%, and preferably, 9.8% to 10.2%. For another example, "about 100° C." refers to 95° C. to 105° C., and preferably, 98° C. to 102° C.

Unless otherwise specified, it must be apparent to a skilled practitioner that the values of peaks from X-ray powder diffraction studies reported in this invention are associated with experimental errors typically observable in this field. Specifically, a peak is interpreted as to be located within ±0.5° of the value reported herein. More specifically, a peak is interpreted as to be located within ±0.2° of the value reported herein.

Crystalline Forms of the Compound of Formula 1

The present invention provides a crystalline form of the compound of Formula 1 below, i.e., N-(3-(2-(4-(4-methyl-piperazin-1-yl)phenylamino)thieno[3,2-d]pyrimidin-4-yloxy)phenyl)acrylamide:

[Formula 1]

The compound of Formula 1 above (free base) may be prepared according to the conventional procedure described in WO 2011/162515, which is hereby incorporated by reference in its entirety.

The compound of Formula 1 may be prepared in a crystalline or amorphous form or a mixture thereof, and preferably in a crystalline form because the crystalline for has excellent stability and non-hygroscopicity, and thus has a physicochemical property which facilitates its formulation.

According to the present invention, the compound of Formula 1 can be prepared in various crystalline forms, and each of the possible crystalline forms will be described in detail herein below.

In one embodiment of the present invention, provided are crystalline forms of the compound of Formula 1. In a particular embodiment of the present invention, these crystalline forms are anhydrous. In another particular embodiment, the crystalline forms are hydrates. In a further specific embodiment, this hydrate is a dihydrate. In yet another specific embodiment, the crystalline form is a trihydrate.

In an exemplary embodiment, the present invention provides a crystalline dihydrate form (Form A) of the compound of Formula 1. Form A exhibits an XRPD pattern comprising peaks at 2θ=8.6°±0.2°, 16.0°±0.2° and 17.2°±0.2° when irradiated with a Cu—Kα light source. More specifically, the crystalline form has an XRPD pattern comprising peaks at diffraction angles of 2θ=8.6°±0.2°, 9.4°±0.2°, 10.3°±0.2°, 13.7°±0.2°, 16.0±0.2°, 17.2°±0.2°, 17.9°±0.2°, 19.7°±0.2°, 22.1°±0.2°, 23.6°±0.2°, and 26.4°±0.2° when irradiated with a Cu—Kα light source. More specifically, the above crystalline form (Form A) of the compound of Formula 1 has an XRPD pattern comprising peaks at diffraction angles of 2θ=8.6°±0.2°, 9.4°±0.2°, 10.3°±0.2°, 13.7°±0.2°, 16.0°±0.2°, 17.2°±0.2°, 17.9°±0.2°, 19.7°±0.2°, 22.1°±0.2°, 22.3°±0.2°, 23.2°±0.2°, 23.6°±0.2°, 26.4°±0.2°, 29.7°±0.2°, and 35.3°±0.2° when irradiated with a Cu—Kα light source. These peaks may be those having a relative intensity ($I/I_o$) of about 20% or more.

The above crystalline form may have an endothermic peak which has a starting point at about 75° C. and its lowest point at about 93° C., an exothermic peak which has a starting point at about 141° C. and its highest point at about 149° C., and an endothermic peak which has a starting point at about 199° C. and its lowest point at about 205° C., in a DSC (10° C./min).

The above crystalline form may have a melting point of about 203° C. To 204° C.

The above crystalline form may have an absorption amount of about 1.5% to 2.5% in the region with a relative humidity of 10% to 90%, in a DVS.

In another exemplary embodiment, the present invention provides a trihydrate crystalline forms (Form B) of the compound of Formula 1. Form B exhibits an XRPD pattern comprising peaks at 2θ=5.3°±0.2° and 16.2°±0.2° when irradiated with a Cu—Kα light source. More specifically, the crystalline form has an XRPD pattern comprising peaks at diffraction angles of 2θ=5.3°±0.2°, 16.2°±0.2°, and 20.7°±0.2° when irradiated with a Cu—Kα light source. More specifically, the above crystalline form (Form B) of the compound of Formula 1 has an XRPD pattern comprising peaks at diffraction angles of 2θ=5.3°±0.2°, 16.2°±0.2°, 20.7°±0.2°, 25.4°±0.2°, and 28.5°±0.2° when irradiated with a Cu—Kα light source. These peaks may be those having a relative intensity ($I/I_o$) of about 7% or more.

The above crystalline form may have an endothermic peak which has a starting point at about 74° C. and its lowest point at about 95° C., an exothermic peak which has a starting point at about 136° C. and its highest point at about 145° C., and an endothermic peak which has a starting point at about 195° C. and its lowest point at about 203° C., in a DSC (10° C./min).

the above crystalline form may have a melting point of about 204° C. to 205° C.

The above crystalline form may have an absorption amount of about 5% to 6% in the region with a relative humidity of 10% to 90%, in a DVS.

In still another exemplary embodiment, the present invention provides an anhydrous crystalline form (Form C) of the compound of Formula 1. Form C exhibits an XRPD pattern comprising peaks at 2θ=3.8°±0.2° and 11.6°±0.2° when irradiated with a Cu—Kα light source. More specifically, the crystalline form has an XRPD pattern comprising peaks at diffraction angles of 2θ=3.8°±0.2°, 9.8°±0.2°, 11.6°±0.2°, 16.9°±0.2°, and 19.8°±0.2° when irradiated with a Cu—Kα light source. More specifically, the above crystalline form (Form C) of the compound of Formula 1 has an XRPD pattern comprising peaks at diffraction angles of 2θ=3.8°±0.2°, 9.8°±0.2°, 11.6°±0.2°, 16.9°±0.2°, 19.8°±0.2°, 20.2°±0.2°, 21.9°±0.2°, 24.3°±0.2°, and 24.7° when irradiated with a Cu—Kα light source. These peaks may be those having a relative intensity ($I/I_o$) of about 7% or more.

The above crystalline form may have an endothermic peak which has a starting point at about 194° C. and its highest point at about 207° C. in a DSC(10° C./min).

The above crystalline form may have a melting point of about 204° C. to 205° C.

The above crystalline form may have an absorption amount of 0.9% to 1.1% in the region with a relative humidity of 10% to 90%, in a DVS.

In still another exemplary embodiment, the present invention also provides an anhydrous crystalline form (Form D) of the compound of Formula 1. Form D exhibits an XRPD pattern comprising peaks at 2θ=11.1°±0.2°, 20.3°±0.2° and 20.8°±0.2° when irradiated with a Cu—Kα light source. More specifically, the crystalline form has an XRPD pattern comprising peaks at diffraction angles of 2θ=11.1°±0.2°, 14.6°±0.2°, 15.5°±0.2°, 20.3°±0.2°, 20.8°±0.2°, 21.0°±0.2°, and 22.2°±0.2° when irradiated with a Cu—Kα light source. More specifically, the above crystalline form (Form D) of the compound of Formula 1 has an XRPD pattern comprising peaks at diffraction angles of 2θ=8.8°±0.2°, 10.5°±0.2°, 11.1°±0.2°, 14.6°±0.2°, 15.5°±0.2°, 17.5°±0.2°, 19.2°±0.2°, 19.4°±0.2°, 20.3°±0.2°, 20.8°±0.2°, 21.0°±0.2°, 22.2°±0.2°, 23.1°±0.2°, 23.4°±0.2°, 25.0°±0.2°, and 25.2°±0.2° when irradiated with a Cu—Kα light source. These peaks may be those having a relative intensity ($I/I_o$) of about 10% or more.

The above crystalline form may have an endothermic peak which has a starting point at about 204° C. and its highest point at about 208° C. in a DSC (10° C./min.

The above crystalline form may have a melting point of about 204° C. to 205° C.

The above crystalline form may have an absorption amount of 0.2% to 0.5% in the region with a relative humidity of 10% to 90%, in a DVS.

Medical Use and Pharmaceutical Composition

As disclosed in WO 2011/162515, the compound of Formula 1 has been shown to be useful for the selective and effective inhibitory activity against the growth of cancer cells and induced by a mutation in epidermal growth factor receptor (EGFR) tyrosine kinase or a mutant thereof, and drug resistance thereof.

In one aspect the invention further provides a crystalline form of the compound of Formula 1 as described herein for use in the treatment of a cancer harboring one or more EGFR mutation.

In a further aspect the invention provides a method for the treatment of cancer comprising administering to a patient in need thereof a therapeutically effective amount of a crystalline form of the compound of Formula 1 as described herein, wherein the cancer to be treated is a cancer harboring one or more EGFR mutation.

In a further aspect the cancer to be treated is a cancer harboring one or more EGFR mutations wherein at least one EGFR mutation is selected from DEll9 (deletion in exon 19), L858R and T790M.

In a further aspect the cancer to be treated is a cancer harboring a Dell9 EGFR mutation.

In a further aspect the cancer to be treated is a cancer harboring the EGFR mutation L858R.

In a further aspect the cancer to be treated is a cancer harboring the EGFR mutation T790M.

In a further aspect the cancer to be treated is a cancer harboring at least two EGFR mutations selected from the group consisting of DEll9/T790M and L858R/T790M.

In this aspect, the crystalline forms of the compound of Formula 1 may be used for the preparation of a pharmaceutical composition for preventing or treating cancers or tumors induced by epidermal growth factor receptor tyrosine kinase of a mutant thereof. The pharmaceutical composition may be used to treat the same cancers harboring EGFR mutation as described for the crystalline forms of the compound of Formula 1 hereinbefore.

Accordingly, the present invention provides a pharmaceutical composition containing a crystalline form of the compound of Formula 1 and at least one pharmaceutically acceptable carrier or diluent. The pharmaceutical composition may be used for the treatment of cancers or tumors induced by epidermal growth factor receptor tyrosine kinase or a mutant thereof.

the administration dose of the crystalline forms of the compound of Formula 1 or a pharmaceutical composition containing the same may vary depending on the subject to be treated, severity of illness or health state of the subject, administration rate, physician's decision, etc., but may be conventionally administered to a human subject having a body weight of e.g. 70 kg via an oral or parenteral administration route in an amount of 10 mg to 2,000 mg as an active ingredients based on the compound of Formula 1, preferably in an amount of 50 mg to 1,000 mg, 1 to 4 times daily or on an on/off schedule. In some cases, it may be more appropriate to administer a lower dosage than that mentioned above, a higher dosage than the above may be administered if it does not cause harmful side effects, and in the case when a significantly larger dosage is to be administered, the administration may be performed daily by several divided doses with a lesser dosage per administration.

The pharmaceutical composition according to the present invention may be prepared in various formulations for oral administration according to the conventional methods, e.g., tablets, pills, powders, capsules, syrups, emulsions, microemulsions, etc., or for parenteral administration, e.g., intramuscular, intravenous, or subcutaneous administrations.

The pharmaceutical composition may contain any conventional non-toxic, pharmaceutically acceptable carrier, diluents, adjuvant, excipient, or vehicle.

When the pharmaceutical composition according to the present invention is prepared as a formulation for oral administration, the carrier to be used may include, e.g., cellulose, calcium silicate, corn starch, lactose, sucrose, dextrose, calcium phosphate, steraic acid, magnesium stearate, calcium sterate, gelatin, talc, surfactants, suspending agents, emulsifying agents, diluents, etc. Additionally, when the pharmaceutical composition is prepared as a formulation for oral administration, the diluents to be used may include lactose, mannitol, saccharide, microcrystalline cellulose, cellulose derivative, corn starch, etc. When the pharmaceutical composition according to the present invention is prepared as a formulation for injections, the carrier to be used may include, e.g., water, saline, an aqueous sugar-like solution, alcohols, ethers (e.g., polyethyleneglycol400), oils, fatty acids, fatty acid esters, glycerides, surfactants, suspending agents, emulsifying agents, etc.

Hereinafter, the present invention will be described in more detail with reference to the following Examples. However, these Examples are for illustrative purposes only, and the invention is not intended to be limited by these Examples.

Analysis Apparatus and Method of Measurement

1. X-ray Powder Diffraction (XRPD)

X-ray powder diffraction (XRPD) analyses of samples were performed in the range from 3° 2θ to 40° 2θ using a D8 Advance (Bruker ASX, Germany) analyzer. When the amount of a given sample was less than 100 mg, about 5 mg to 10 mg of the sample was gently compressed on a glass slide which was fit into a sample holder. When the amount of a given sample was greater than 100 mg, about 100 mg of the sample was gently compressed in a plastic sample holder so that the sample surface became flat and positioned immediately on top of the sample holder level.

the measurement was performed as follows:
Anode material (Kα): Cu—Kα (1.54056 Å)
Scan range: 3° to 40°
Generator settings: 100 mA, 40.0 kV
Scan speed: 1 sec/step
Diver slit: 0.3°
Anti-scatter slit: 0.3°
Temperature: 20° C.
Step size: 0.02° 2θ
Rotation: use
Goniometer radius: 435 mm 2. Differential Scanning Calorimeter (DSC)

Differential scanning calorimeter (DSC) analysis was performed in as STA-1000 (Scinco, Korea) at 30° C. to 350° C. A sample in an amount of 5 mg to 10 mg was weighed and added into an aluminum DSC fan, and the fan was scaled with a perforated aluminum lid in a non-sealing manner. Then, the sample was heated at a scan speed of 10° C./min from 30° C., and the heat flow reaction generated was monitored in a DSC.

3. Dynamic Vapor Sorption (DVS)

Dynamic vapor sorption (DVS) analysis was performed in a DVS advantage (Surface measurement system, United Kingdom) analyzer at 25° C. with a relative humidity of 0% to 90%. A sample in an amount of 10 mg was placed into a wire-mesh vapor sorption balance pan and then attached to a DVS advantage dynamic vapor sorption balance via surface measurement systems. Until a stable weight was achieved (99.5% completion of steps), the sample was applied to a ramping profile with a relative humidity of 10% to 90% with a 10% increase of the sample while maintaining the sample in each step. Upon completion of the sorption cycle, the sample was dried using the same process while maintaining a relative humidity of below 0%. The changes in the sample weight during the adsorption/desorption cycle (repeated 3 times) were recorded and the hygroscopicity of the sample was measured.

4. High Performance Liquid Chromatography (HPLC)

High performance liquid chromatography (HPLC) analysis was performed for the purposes of analyzing purity and contents such as a stability test, etc., using an Agilent 1100/1200 series HPLC Systems (Agilent, USA) analyzer, and the conditions used for HPLC were as follows.

Purity and Content Analysis Conditions: Thienopyrimidine Compound of Formula 1
Column: Hydrosphere C18 (YMC), 5 μm (150 mm×4.6 mm)
Column temperature: 30° C.
Detector: UV spectrophotometer
Detection wavelength: 254 nm
Flow rate: 1.0 mL/min
Time of analysis: 35 min
Eluent: $NaClO_4$—$NaH_2PO_4$—phosphate buffer solution (pH 2.5±0.1)/$CH_3CN$=40/60 (v/v %)

5. Karl-Fischer Titrator: Metrohm, 795KFT Titrino

6. Melting Point Analyzer: Bastead electro thermal, 9300

7. Nuclear Magnetic Resonance (NMR): BRUKER, Advance DPX 300 (300 MHz)

Preparation of crystalline forms of a compound of Formula 1

Comparative Example 1: Preparation of an Amorphous Form of a Compound of Formula 1

An amorphous form of the compound of Formula 1 was obtained according to the method disclosed in WO 2011/162515, or a similar method thereof, which is reference herein.

Water content: 0.3%
Melting point: 203° C. to 205° C.
MS Spectrum: m/z=487.19 (M+1)
$^1$H-NMR Spectrum (300 MHz, DMSO-$d_6$) δ 10.37 (s, 1H), 9.24 (s, 1H), 8.27 (d, 1H), 7.71 (d, 1H), 7.64 (d, 1H), 7.49-7.41 (m, 3H), 7.32 (d, 1H), 7.07 (dd, 1H), 6.71 (d, 2H), 6.42 (dd, 1H), 6.28 (dd, 1H), 5.78 (dd, 1H), 2.99 (t, 4H), 2.21 (s, 3H).

Analysis of Characteristics

Figure 1A:
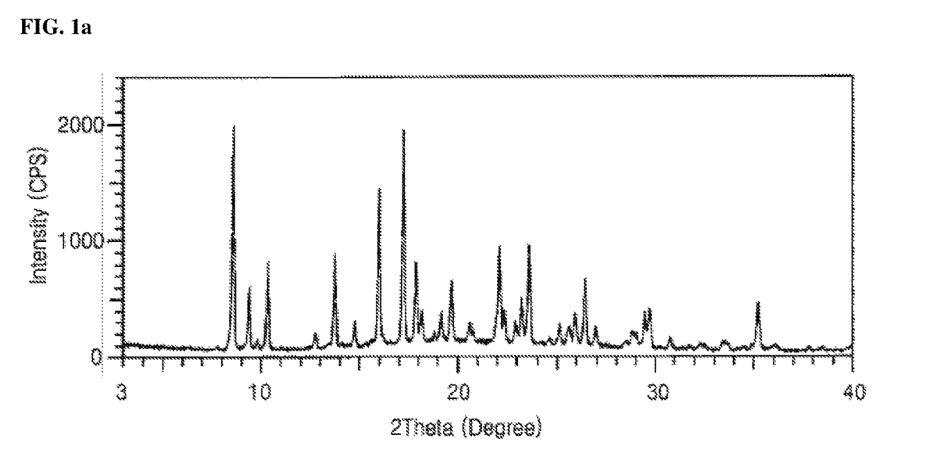
FIGS. 1a to 1d show X-ray powder diffraction (XRPD) patterns of crystalline forms of the compound of Formula 1 prepared in Examples 1 to 4 of the present invention.
Figure 1B:
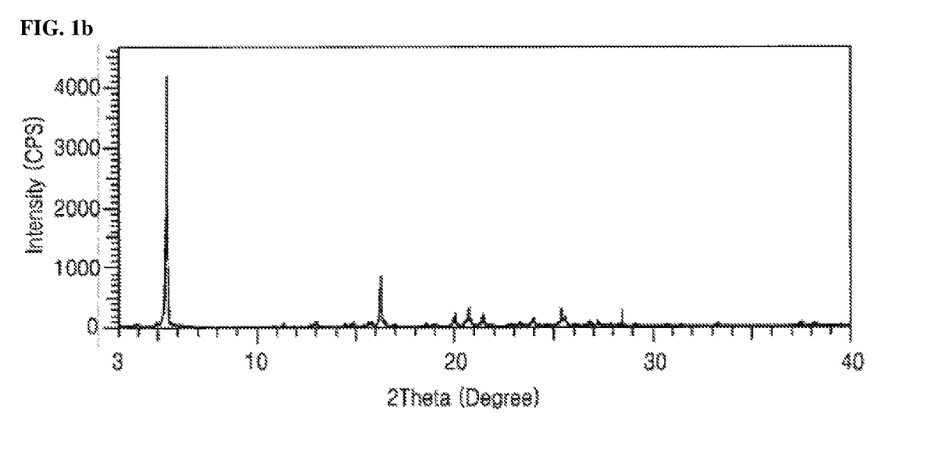
Figure 1C:
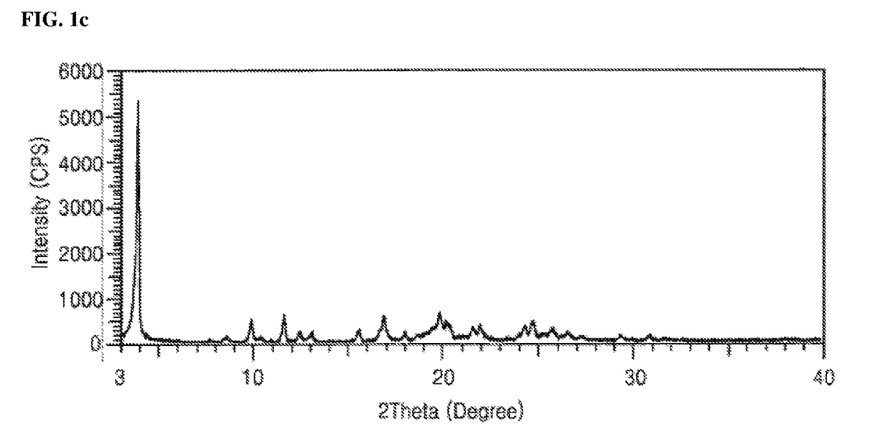
Figure 1D:
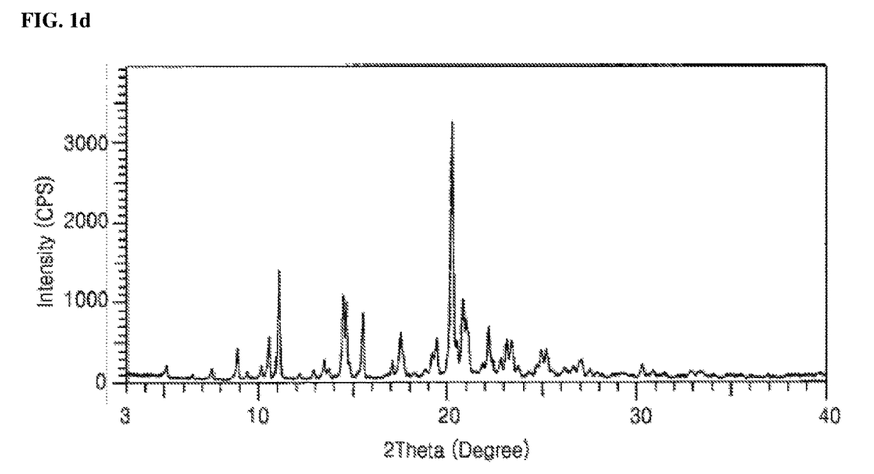
Figure 1E:
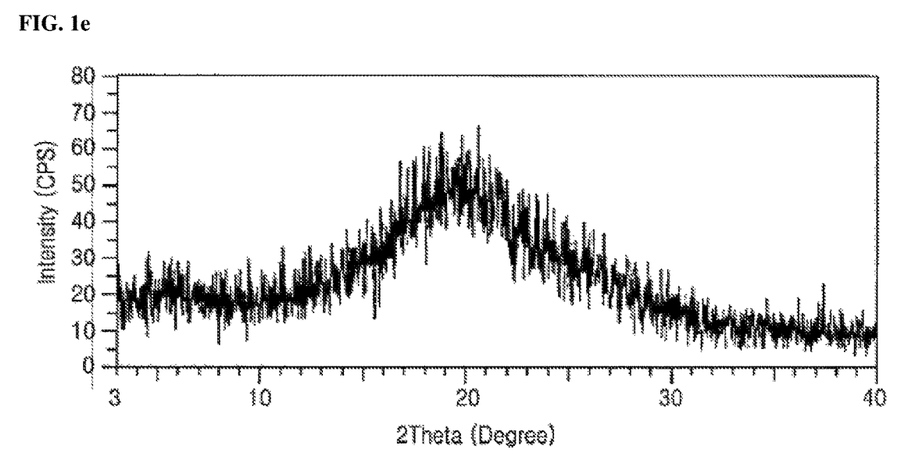
FIG. 1e shows an X-ray powder diffraction (XRPD) pattern of an amorphous form of the compound of Formula 1 prepared in Comparative Example 1 of the present invention.
Figure 2A:
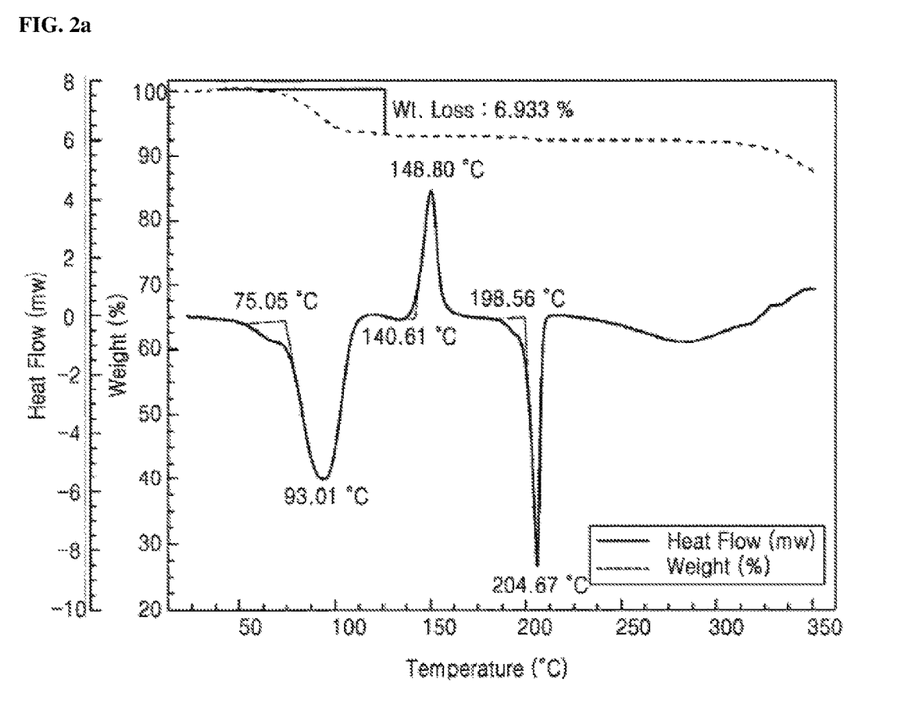
FIGS. 2a to 2d show the graphs of differential scanning calorimetry (DSC) of crystalline forms of the compound of Formula 1 prepared in Examples 1 to 3 of the present invention.
Figure 2B:
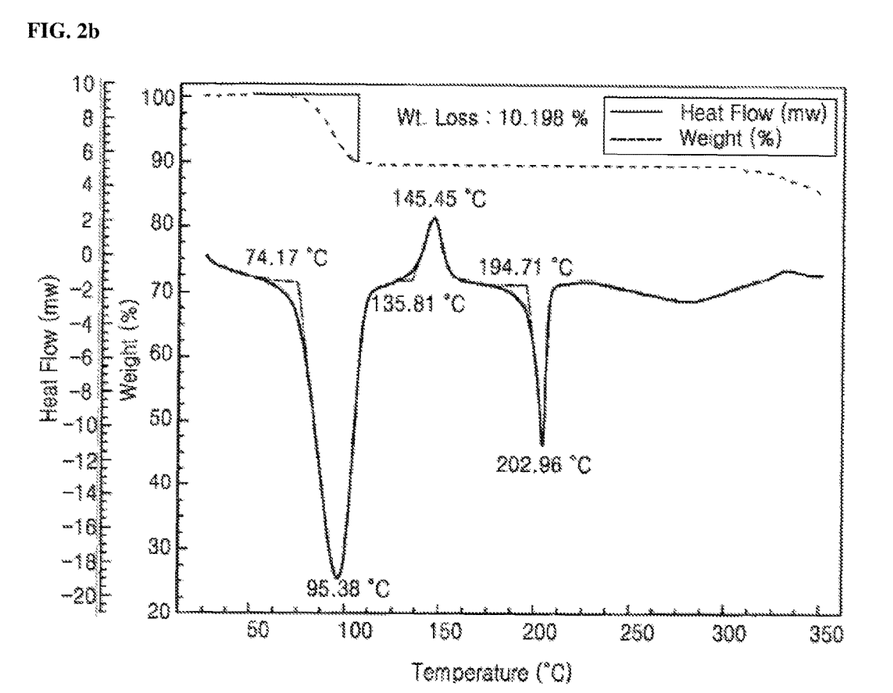
Figure 2C:
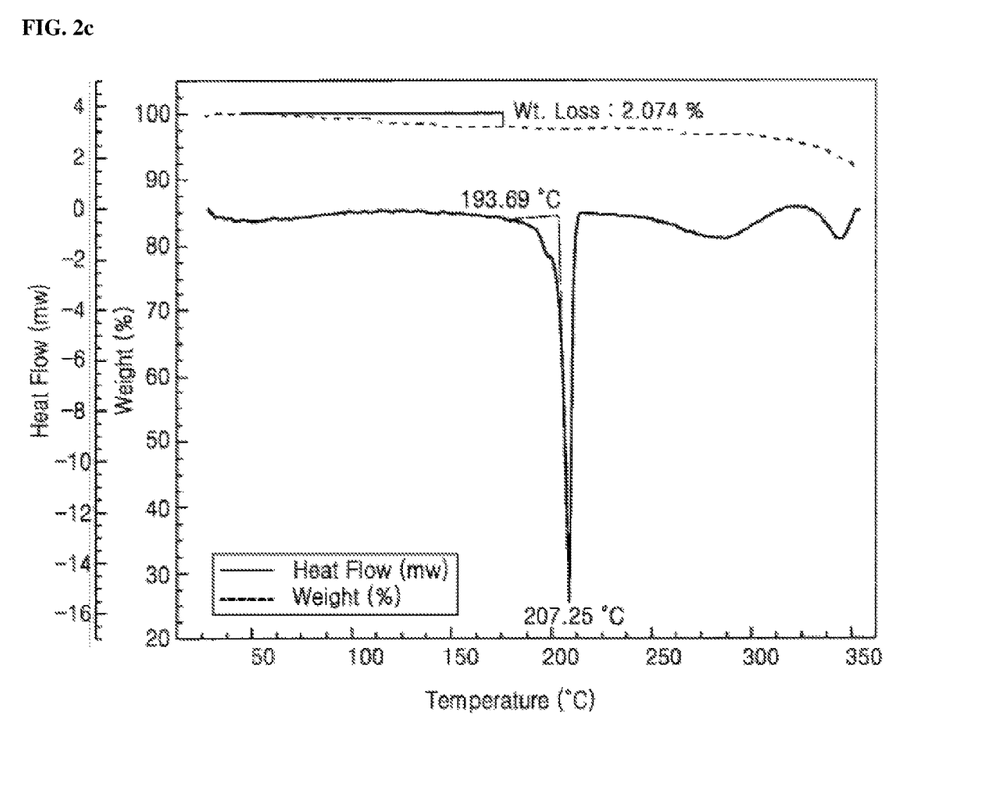
Figure 2D:
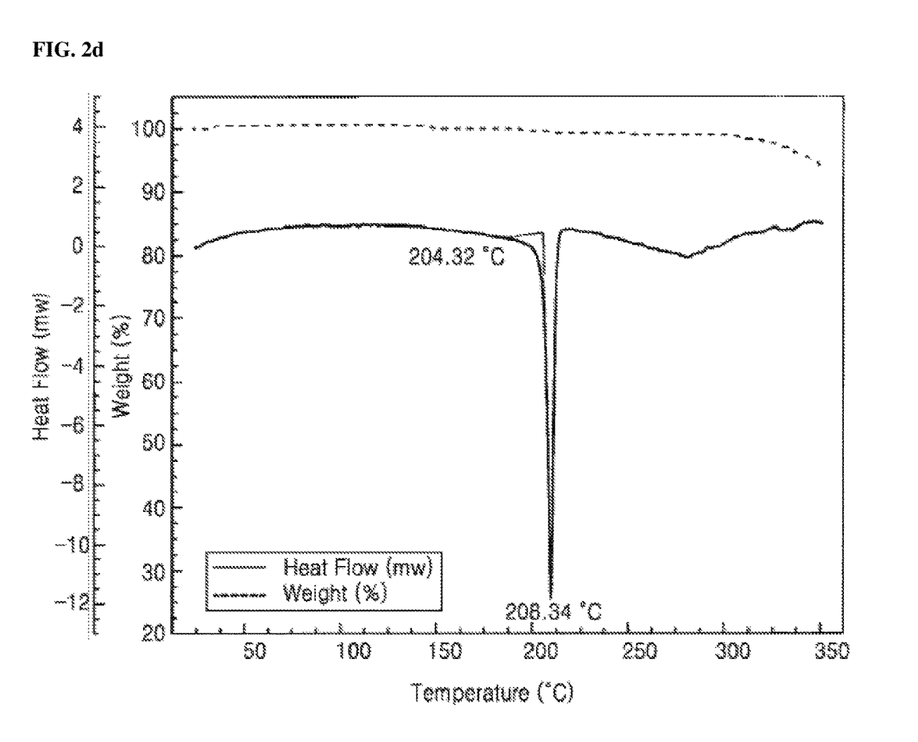
Figure 2E:
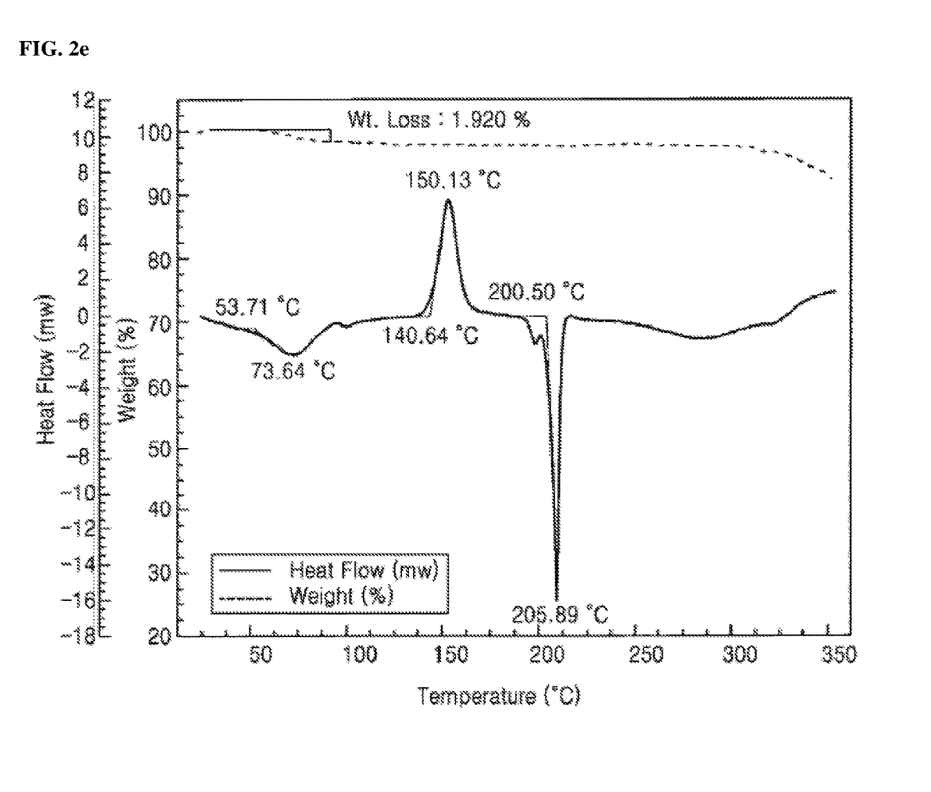
FIG. 2e shows the graph of differential scanning calorimetry (DSC) of an amorphous form of the compound of Formula 1 prepared in Comparative Example 1 of the present invention.
Figure 3A:
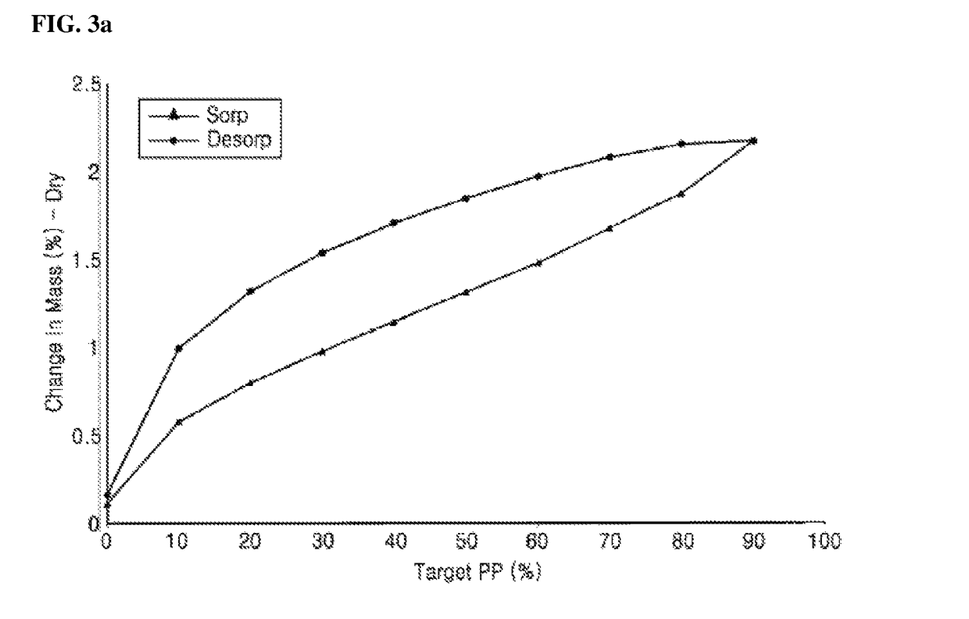
FIGS. 3a to 3d show the graphs of dynamic vapor sorption (DVS) of crystalline forms of the compound of Formula 1 prepared in Examples 1 to 3 of the present invention.
Figure 3B:
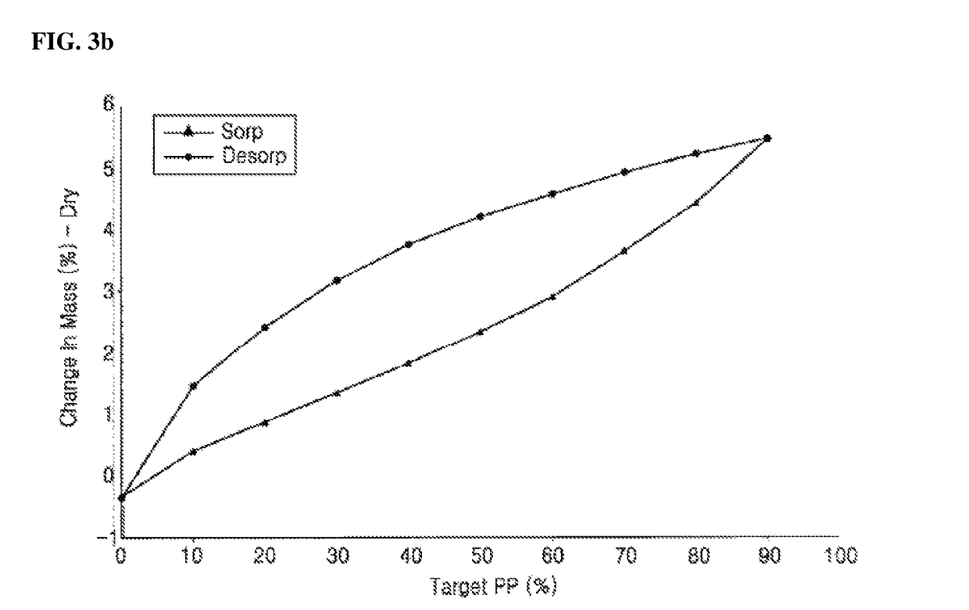
Figure 3C:
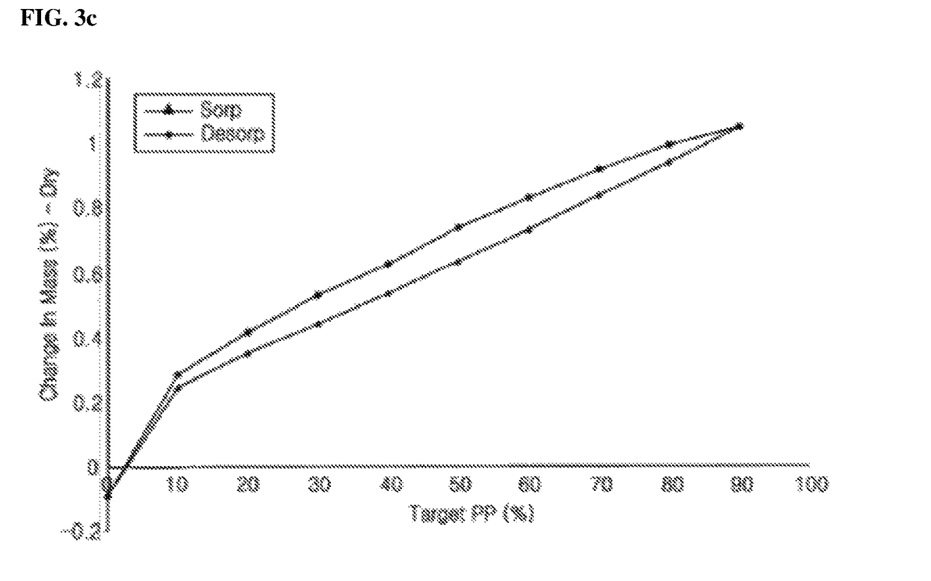
Figure 3D:
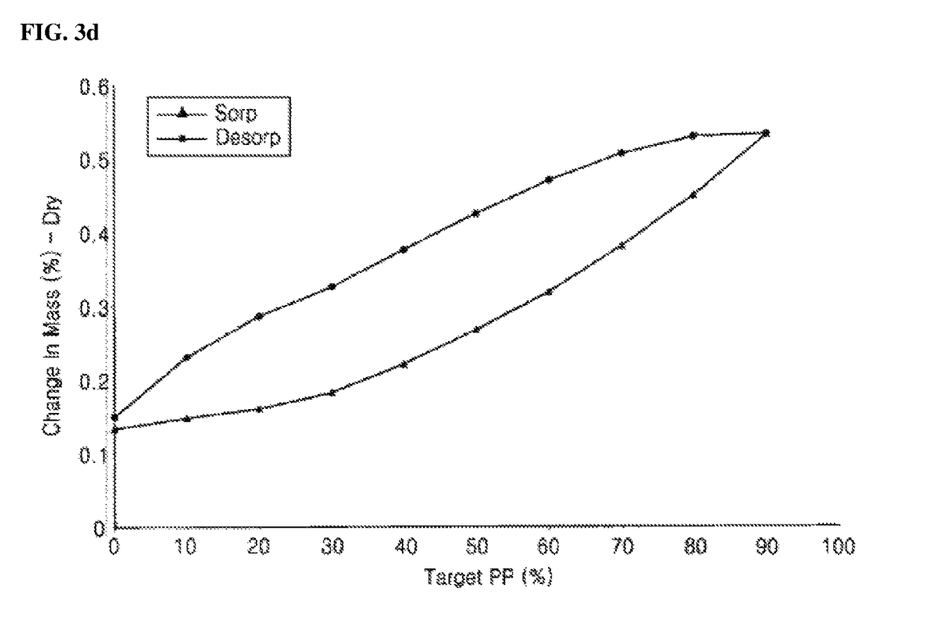
Figure 3E:
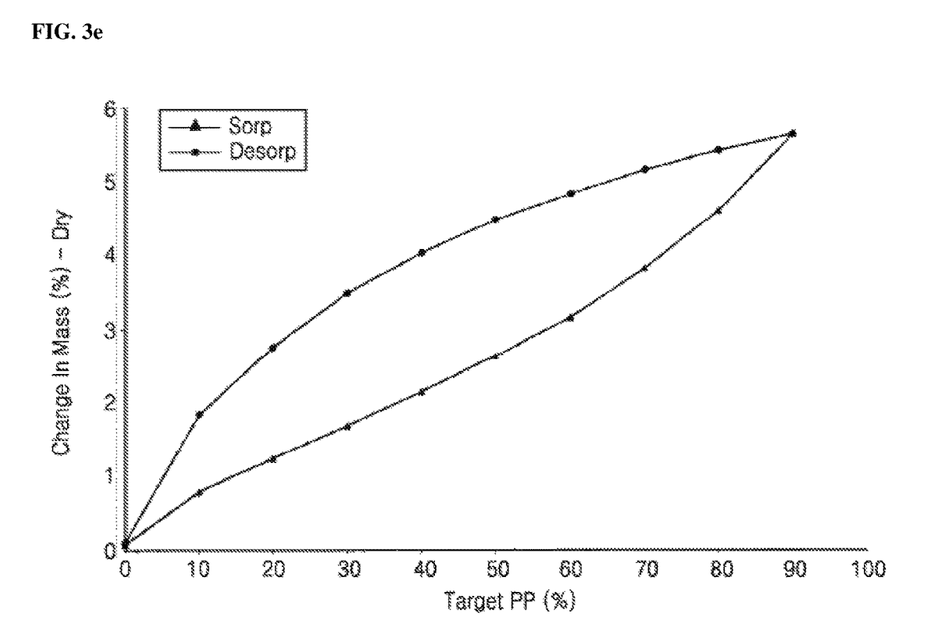
FIG. 3e shows the graph of dynamic vapor sorption (DVS) of an amorphous form of the compound of Formula 1 prepared in Comparative Example 1 of the present invention.

The results of XRPD, DSC, and DVS analyses of the amorphous form prepared in Comparative Example 1 are shown in FIGS. 1e, 2e, and 3e, respectively.

The amorphous form did not show any particular diffraction value in the XRPD pattern.

Additionally, the amorphous form was shown to have an endothermic peak which has a starting point at about 53.7° C. and its highest point at about 73.64° C., and an exothermic peak which has a starting point at about 140.64° C. and its highest point at about 150.13° C., in a DSC (10° C./min), and this was expected to be a phase transition. An endothermic peak was shown at about 205.89° C.

In the DSC, the endothermic peak at about 73.64° C. indicates the dehydration point, and the endothermic peak at about 205.89° C. indicates a melting point. The melting point was measured to be between about 204° C. and about 205° C.

Additionally, in the DVS, the amorphous form showed a continuous hygroscopic tendency in the region with a relative humidity of 10% to 90% up to a water content between about 5% and about 6%, and this is expected to be unstable from the hygroscopic aspect.

Example 1: Preparation of a Crystalline Form (Form A) of a Compound of Formula 1

The title compound prepared in Comparative Example 1 (100 g; 0.21 mol) was added into a mixed solvent of acetone (400 mL) and water (100 mL), and the mixture was heated under reflux for 2 hours. Then, the resultant was cooled to 15° C. to 20° C. or below, stirred for 12 hours, and the resulting solids were filtered, washed with a mixed solvent (acetone/water=4/1), and dried at 50° C. to obtain the compound of Formula 1 in a crystalline form (78 g, yield: 78%).

Water content: 7.0% (theoretical value of a dihydrate: 6.90%)

Analysis of Characteristics

The results of XRPD, DSC, and DVS analyses of the crystalline form prepared in Example 1 are shown in FIGS. 1a, 2a, and 3a, respectively.

The peaks having a relative intensity ($I/I_o$) of 3% or higher in the XRPD pattern of the above crystalline form are shown in Table 1 below. When the peaks had $I/I_o$ ratios equal to or higher than 2.0%, they appeared at diffraction angles of 8.6°, 9.4°, 10.3°, 13.7°, 16.0°, 17.2°, 17.9°, 19.7°, 22.1°, 22.3°, 23.2°, 23.6°, 26.4°, 29.7°, and 35.3° (2θ±0.2°).

TABLE 1

| 2Θ (±0.2) | d | $I/I_o$ (%) |
|---|---|---|
| 8.6 | 10.3 | 100 |
| 9.4 | 9.4 | 29.5 |
| 10.3 | 8.6 | 41.1 |
| 12.7 | 7.0 | 10 |
| 13.7 | 6.4 | 44.4 |
| 14.7 | 6.0 | 15.3 |
| 16.0 | 5.5 | 72.4 |
| 17.2 | 5.1 | 97.8 |
| 17.9 | 5.0 | 41 |
| 18.1 | 4.9 | 19.8 |
| 19.2 | 4.6 | 19.3 |
| 19.7 | 4.5 | 32.3 |
| 20.6 | 4.3 | 15.1 |
| 22.1 | 4.0 | 47.8 |
| 22.3 | 4.0 | 20.2 |
| 22.9 | 3.9 | 15.3 |
| 23.2 | 3.8 | 26.3 |

TABLE 1-continued

| 2Θ (±0.2) | d | $I/I_o$ (%) |
|---|---|---|
| 23.6 | 3.8 | 47.9 |
| 25.1 | 3.5 | 14.0 |
| 25.6 | 3.5 | 12.9 |
| 25.9 | 3.4 | 18.9 |
| 26.4 | 3.4 | 33.6 |
| 27.0 | 3.3 | 12.4 |
| 28.8 | 3.1 | 10.7 |
| 29.5 | 3.0 | 19.3 |
| 29.7 | 3.0 | 20.8 |
| 30.1 | 2.9 | 8.4 |
| 35.3 | 2.5 | 23.1 |

2Θ: diffraction angle, d: distance between crystal faces, $I/I_o$ (%): relative intensity (I indicates the intensity of each peak; $I_o$ indicates the intensity of the highest peak.)

Additionally, the above crystalline form showed an endothermic peak which has a starting point at about 75.05° C. and its highest point at about 93.01° C., and an exothermic peak which has a starting point at about 140.61° C. and its highest point at about 148.80° C. in a DSC (10° C./min), and this was expected to be a phase transition. Additionally, an endothermic peak which has a starting point at about 198.56° C. and its highest point at about 204.67° C. was shown.

In the DSC, the endothermic peak at about 93.01° C. indicates the dehydration point, and the endothermic peak at about 204.67° C. indicates a melting point. The melting point was measured to be between about 203° C. and about 204° C.

Additionally, in the DVS, the above crystalline forms showed a continuous hygroscopic tendency in the region with a relative humidity of 10% to 90% up to a water content of about 1.5%, and this is expected to be stable from the hygroscopic aspect.

Example 2: Preparation of a Crystalline Form (Form B) of a Compound of Formula 1

The amorphous form of the compound of Formula 1 prepared in Comparative Example 1 (200 g; 0.42 mol) was added into a mixed solvent of acetone (2.2 L) and water (200 mL), and the mixture was dissolved by heating at 60° C. for 1 hour. Then, the resultant was treated with active carbon, filtered with celite, and washed with acetone (400 mL).

The filtrate solution, at between 30° C. and 40° C. was treated with water (600 mL), cooled slowly to room temperature, stored for 3 hours, cooled again to a temperature between 5° C. and 10° C., and stirred for 2 hours.

The thus-formed solids were filtered, washed with a mixed solvent (300 mL) of acetone and water (v/v=2.5/1), and dried at 50° C. to obtain the compound of Formula 1 in a crystalline form (152.0 g, yield: 76.0%).

Water content: 9.8% (theoretical value of a trihydrate: 10.0%)

Analysis of Characteristics

The results of XRPD, DSC, and DVS analyses of the crystalline form prepared in Example 2 are shown in FIGS. 1b, 2b, and 3b, respectively.

The peaks having a relative intensity ($I/I_o$) of 3% or higher in the XRPD pattern of the above crystalline forms are shown in Table 2 below. When the peaks had $I/I_o$ ratios equal to or higher than 7%, they appeared at diffraction angles of 5.3°, 16.2°, 20.7°, 25.4°, and 28.5° (2θ±0.2°).

TABLE 2

| 2Θ (±0.2) | d | I/I$_o$ (%) |
|---|---|---|
| 5.3 | 16.5 | 100 |
| 16.2 | 5.5 | 20.5 |
| 20.7 | 4.3 | 7.6 |
| 21.4 | 4.1 | 5.2 |
| 24.0 | 3.7 | 3.7 |
| 25.4 | 3.5 | 7.4 |
| 28.5 | 3.1 | 7.0 |

2Θ: diffraction angle, d: distance between crystal faces, I/I$_o$ (%): relative intensity (I indicates the intensity of each peak; I$_o$ indicates the intensity of the highest peak.)

Additionally, the above crystalline form showed an endothermic peak which has a starting point at about 74.17° C. and its lowest point at about 95.38° C., and an exothermic peak which has a starting point at about 135.81° C. and its highest point at about 145.45° C., in a DSC (10° C./min), and this was expected to be a phase transition. Additionally, an endothermic peak which has a starting point at about 194.71° C. and its highest point at about 202.96° C. was shown.

In the DSC, the endothermic peak at about 95.38° C. indicates the dehydration point of the crystalline form of dehydrate of the compound of Formula 1, and the endothermic peak at about 194.71° C. indicates a melting point. The melting point was measured to be between about 204° C. and about 205° C.

Additionally, in the DVS, the above crystalline forms showed a hygroscopic tendency in the region with a relative humidity of 10% to 90% up to a water content between about 5% and about 5.5%.

Example 3: Preparation of a Crystalline Form (Form C) of a Compound of Formula 1

The title compound (5.0 g) obtained in Comparative Example 1 was dried at 170° C. using a weight-reducing drying device (LOD) for 30 minutes to remove water, and the compound of Formula 1 was obtained in a crystalline form.

Analysis of Characteristics

The results of XRPD, DSC, and DVS analyses of the crystalline form prepared in Example 3 are shown in FIGS. 1c, 2c, and 3c, respectively.

The peaks having a relative intensity (I/I$_o$) of 3% or higher in the XRPD pattern of the above crystalline forms are shown in Table 3 below. When the peaks had I/I$_o$ ratios equal to or higher than 7%, they appeared at diffraction angles of 3.8°, 9.8°, 11.6°, 16.9°, 19.8°, 20.2°, 21.9°, 24.3°, and 24.7° (2θ±0.2°).

TABLE 3

| 2Θ (±0.2) | d | I/I$_o$ (%) |
|---|---|---|
| 3.8 | 23.1 | 100 |
| 8.5 | 10.4 | 3.0 |
| 9.8 | 9.0 | 10.0 |
| 11.6 | 7.6 | 12.2 |
| 12.4 | 7.1 | 4.5 |
| 13.0 | 6.8 | 3.7 |
| 15.5 | 5.7 | 4.9 |
| 16.9 | 5.3 | 11.0 |
| 18.0 | 4.9 | 3.6 |
| 18.7 | 4.8 | 3.2 |
| 19.5 | 4.6 | 6.2 |
| 19.8 | 4.5 | 13.0 |
| 20.2 | 4.4 | 9.4 |
| 21.6 | 4.1 | 5.8 |
| 21.9 | 4.0 | 8.1 |

TABLE 3-continued

| 2Θ (±0.2) | d | I/I$_o$ (%) |
|---|---|---|
| 24.0 | 3.7 | 4.3 |
| 24.3 | 3.7 | 7.2 |
| 24.7 | 3.6 | 9.1 |
| 25.3 | 3.5 | 3.8 |
| 25.7 | 3.5 | 5.8 |
| 26.5 | 3.4 | 4.5 |
| 30.9 | 2.9 | 3.4 |

2Θ: diffraction angle, d: distance between crystal faces, I/I$_o$ (%): relative intensity (I indicates the intensity of each peak; I$_o$ indicates the intensity of the highest peak.)

Additionally, the above crystalline form showed an endothermic peak which has a starting point at about 193.69° C. and its highest point at about 207.25° C. in a DSC (10° C./min). In the DSC, the endothermic peak indicates the dehydration point. The melting point was measured to be between about 204° C. and about 205° C.

Additionally, in the DVS, the above crystalline form showed the hygroscopic level of about 0.8% to about 0.8% in the region with a relative humidity of 10% to 90%. From these results, the above crystalline forms were expected to be very stable from the hygroscopic aspect. Additionally, from these results, it was confirmed that they were very stable under a long-term storage condition (a temperature of 25° C. and a relative humidity of 60%) and an accelerated condition (a temperature of 40° C. and a relative humidity of 75%).

Example 4: Preparation of a Crystalline Form (Form D) of a Compound of Formula 1

The title compound (5.0 g) obtained in Examples 1 and 2 were added into isopropanol (50 mL) and heated under reflux for 2 hours. Then, the reaction mixture was cooled to room temperature and stirred for 3 hours, and the resulting solids were filtered, washed with isopropanol (10 mL), dried at 50° C., and the compound of Formula 1 was obtained in an crystalline form (3.7 g, yield: 74%).

Water content: 0.2%

Analysis of Characteristics

The results of XRPD, DSC, and DVS analyses of the crystalline form prepared in Example 4 are shown in FIGS. 1d, 2d, and 3d, respectively.

The peaks having a relative intensity (I/I$_o$) of 5% or higher in the XRPD pattern of the above crystalline forms are shown in Table 4 below. When the peaks had I/I$_o$ ratios equal to or higher than 10%, they appeared at diffraction angles of 8.8°, 10.5°, 11.1°, 14.6°, 15.5°, 17.5°, 19.2°, 19.4°, 20.3°, 20.8°, 21.0°, 22.2°, 23.1°, 23.4°, 25.0°, and 25.2° (2θ±0.2°).

TABLE 4

| 2Θ (±0.2) | d | I/I$_o$ (%) |
|---|---|---|
| 5.0 | 17.5 | 6.6 |
| 7.5 | 11.8 | 5.1 |
| 8.8 | 10.0 | 12.9 |
| 10.1 | 8.7 | 6.5 |
| 10.5 | 8.4 | 17.2 |
| 11.1 | 8.0 | 42.6 |
| 13.4 | 6.6 | 8.6 |
| 14.6 | 6.1 | 27.5 |
| 15.5 | 5.7 | 26.1 |
| 17.0 | 5.2 | 7.4 |
| 17.5 | 5.1 | 18.7 |
| 19.2 | 4.6 | 11.6 |
| 19.4 | 4.6 | 15.7 |
| 20.3 | 4.4 | 100 |
| 20.8 | 4.3 | 31.4 |

TABLE 4-continued

| 2Θ (±0.2) | d | I/I₀ (%) |
|---|---|---|
| 21.0 | 4.2 | 22.5 |
| 21.9 | 4.1 | 7.6 |
| 22.2 | 4.0 | 21.3 |
| 22.8 | 3.9 | 9.2 |
| 23.1 | 3.8 | 16.6 |
| 23.4 | 3.8 | 15.7 |
| 23.7 | 3.7 | 6.0 |
| 24.7 | 3.6 | 6.8 |
| 25.0 | 3.6 | 12.4 |
| 25.2 | 3.5 | 12.6 |
| 26.2 | 3.4 | 5.4 |
| 26.6 | 3.3 | 5.8 |
| 27.0 | 3.3 | 8.0 |
| 27.5 | 3.2 | 4.8 |
| 30.3 | 2.9 | 6.6 |

2Θ: diffraction angle, d: distance between crystal faces, I/I₀ (%): relative intensity (I indicates the intensity of each peak; I₀ indicates the intensity of the highest peak.)

Additionally, the above crystalline form showed an endothermic peak which has a starting point at about 204.32° C. and its highest point at about 208.34° C. in a DSC (10° C./min). In the DSC, the endothermic peak indicates the melting point. The melting point was measured to be between about 205° C. and about 207° C.

Additionally, in the DVS, the above crystalline form showed the hygroscopic level of about 0.2% to about 0.5% in the region with a relative humidity of 10% to 90%. From these results, the above crystalline forms were expected to be very stable in terms of hygroscopicity. Additionally, from these results, it was confirmed that they were very stable under a long-term storage condition (a temperature of 25° C. and a relative humidity of 60%) and an accelerated condition (a temperature of 40° C. and a relative humidity of 75%).

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A crystalline form of the compound of Formula 1 shown below, wherein the crystalline form is a dihydrate crystalline form having an X-ray powder diffraction (XRPD) pattern comprising peaks at diffraction angle 2θ values of 8.6°±0.2°, 16.0°+0.2° and 17.2°+0.2° when irradiated with a Cu-Kα light source:

[Formula 1]

2. The crystalline form of claim 1, wherein the crystalline form further comprises peaks at diffraction angle 2θ values of 9.4°±0.2°, 10.3°+±0.2°, 13.7°±0.2°, 17.9°±0.2°, 19.7°±0.2°, 22.1°±0.2°, 23.6°±0.2°, and 26.4°±0.2° when irradiated with a Cu-Kα light source.

3. A crystalline form of the compound of Formula 1 shown below, wherein the crystalline form is a trihydrate crystalline form having an X-ray powder diffraction pattern comprising peaks at diffraction angle 2θ values of 5.3°±0.2° and 16.20°±0.2° when irradiated with a Cu-Kα light source:

[Formula 1]

4. The crystalline form of claim 3, wherein the crystalline form further comprises peaks at diffraction angle 2θ values of 20.7°±0.2°, 25.4°±0.2°, and 28.5°±0.2° when irradiated with a Cu-Kα light source.

5. A crystalline form of the compound of Formula 1 shown below, wherein the crystalline form is an anhydrous crystalline form having an X-ray powder diffraction pattern comprising peaks at diffraction angle 2° values of 3.8θ±0.2° and 11.6°±0.2° when irradiated with a Cu-Kα light source:

[Formula 1]

6. The crystalline form of claim 5, wherein the crystalline form further comprises peaks at diffraction angle 2θ values of 9.8°±0.2°, 16.9°±0.2°, and 19.8°±0.2° when irradiated with a Cu-Kα light source.

7. A crystalline form of the compound of Formula 1 shown below, wherein the crystalline form is an anhydrous crystalline form having an X-ray powder diffraction pattern comprising peaks at diffraction angle 2θ values of 11.1°±0.2°, 20.3°±0.2° and 20.8°±0.2° when irradiated with a Cu-Kα light source:

[Formula 1]

8. The crystalline form of claim 7, wherein the crystalline form further comprises peaks at diffraction angle 2θ values of 14.6°±0.2°, 15.5°±0.2°, 21.0°±0.2°, and 22.2°±0.2° when irradiated with a Cu-Kα light source.

9. The crystalline form of claim 1, wherein the crystalline form is substantially pure.

10. A pharmaceutical composition comprising a crystalline form according to claim 1 and at least one pharmaceutically acceptable carrier or diluent.

11. The pharmaceutical composition of claim 10, wherein the pharmaceutical composition is used for treating cancer induced by epidermal growth factor receptor tyrosine kinase or a mutant thereof.

12. The crystalline form of claim 2, wherein the crystalline form is substantially pure.

13. The crystalline form of claim 3, wherein the crystalline form is substantially pure.

14. The crystalline form of claim 4, wherein the crystalline form is substantially pure.

15. The crystalline form of claim 5, wherein the crystalline form is substantially pure.

16. The crystalline form of claim 6, wherein the crystalline form is substantially pure.

17. The crystalline form of claim 7, wherein the crystalline form is substantially pure.

18. The crystalline form of claim 8, wherein the crystalline form is substantially pure.

* * * * *